US00PP22981P2

(12) United States Plant Patent
Egger

(10) Patent No.: US PP22,981 P2
(45) Date of Patent: Aug. 21, 2012

(54) ***TRADESCANTIA* PLANT NAMED 'LUCKY CHARM'**

(50) Latin Name: ***Tradescantia Andersoniana* Group**
Varietal Denomination: Lucky Charm

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/068,991

(22) Filed: May 24, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(74) *Attorney, Agent, or Firm* — Klarquist Sparkman, LLP

(57) ABSTRACT

A new and distinct cultivar of *Tradescantia* plant characterized by yellow gold to yellow green foliage, purple blue flowers, a compact clumping habit, and excellent vigor.

1 Drawing Sheet

Botanical denomination: *Tradescantia Andersoniana* Group.

Variety designation: 'Lucky Charm'.

BACKGROUND OF THE INVENTION

The present invention relates to a new and distinct cultivar of *Tradescantia*, given the name, 'Lucky Charm'. *Tradescantia* is in the family Commelinaceae. This new variety is from a planned breeding cross for yellow foliage, compact *Tradescantia*. The new cultivar is a seedling from the cross of *Tradescantia* 27-2, a proprietary, unnamed seedling, as the seed parent and *Tradescantia* 28-2 another proprietary, unnamed seedling, as the pollen parent. Compared to the seed parent, *Tradescantia* 27-3, the new cultivar has lavender purple blue rather than dark pink. Compared to the pollen parent, *Tradescantia* 28-2, the new cultivar has yellow gold to yellow green foliage rather than green foliage. Compared to *Tradescantia* 'Blue and Gold' (syn. 'Sweet Kate', unpatented), the new cultivar has a more compact habit.

This plant exhibits the following characteristics that make it unique:

1. a compact clumping habit,
2. yellow gold to yellow green foliage,
3. purple blue flowers,
4. and excellent vigor.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING:

The drawing shows a two-year-old *Tradescantia* 'Lucky Charm' growing in the field in late spring in Canby, Oreg.

DETAILED PLANT DESCRIPTION

The following is a detailed description of the new *Tradescantia* cultivar based on observations of one-year-old specimens grown outside in full sun in gallon container in the nursery in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form*.—Upright clumping.
*Type*.—Herbaceous perennial.
*Cold hardiness*.—USDA Zone 4-9.
*Size*.—Grows to 43 cm wide and 19 cm tall to the top of the foliage and flowers.
*Vigor*.—Excellent.
*Stem*.—Flowering, oval in cross section, swollen at nodes and leafy, grows to 8 mm wide and 17 cm tall to the last leaf, glabrous, internodes range from 1.5 cm to 7.5 cm long, Yellow Green 144A.
*Roots*.—Thick and fleshy, plants root easily from nodes or crown division.

Leaf:

*Type*.—Simple.
*Arrangement*.—Alternate.
*Shape*.—Linear-lanceolate.
*Venation*.—Parallel.
*Leaf description*.—Grows to 24 cm long and 17 mm wide, entire, glabrous inside and out except near base where villous on margin, entire, tip acuminate, base perfoliate.
*Leaf color*.—Varies with light, top and bottom side, ranges from Yellow 10A near the tip to Yellow Green 144A at the base.

Inflorescence:

*Type*.—Terminal umbel-like cyme subtended by 1 or 2 leafy bracts (smaller than the leaves, otherwise the similar, grow to 18 cm long, 16 mm wide, linear lanceolate, top and bottom side Yellow 10A near the tip to Yellow Green 144A at the base).
*Number of flowers per cyme*.—Up to 36.
*Size of inflorescence*.—5 cm tall and 6 cm wide.
*Peduncle*.—None.

*Pedicel.*—20 mm long and 1.2 mm wide, glabrous, flattened, Greyed Purple N187D.

*Bloom period.*—Late May through July in Canby, Oreg.

Flower bud:

*Size.*—12 mm long and 6 mm wide at the widest point prior to opening.

*Description.*—Ovoid.

*Surface texture.*—Pubescent.

*Color.*—Yellow Green 145A.

Flower:

*Type.*—Actinomorphic to irregular, single.

*Size.*—42 mm wide and 10 mm to 16 mm deep.

*Corolla description.*—3 petals, each broadly ovate in shape, 22 mm wide and 22 mm long, margins somewhat undulate, entire on sides with top ⅓ sometimes with small lobes, tip variable from obtuse to notched to lobed, base truncate, glabrous on both sides, top side Violet N88A except center base where N87A, bottom side Violet N88C to Violet N88A on edges.

*Calyx description.*—3 sepals, 12 mm long and 6 mm wide, pubescent outside and glabrous inside, ovate, cupped, entire, acute, Yellow Green 144A inside and out, margins Greyed Purple 187B.

*Pistil description.*—1 in number, 10 mm long, ovary 3 mm long, Yellow Green 145D, style 7 mm long, Violet 87A; stigma White NN155A.

*Stamen description.*—6 in number, 10 mm long, filaments 8 mm long and to 6 mm wide with long hairs, filaments and hairs Violet N88A, anthers reniform in shape, 1 mm long, Yellow 13A, pollen not seen.

*Fragrance.*—None.

*Lastingness.*—A cyme blooms for about 4 weeks on the plant.

Fruit/seed: Fruit a 3-valved, 3-loculed capsule, 1 seed found for 200 flowers, extremely low fertility, seeds oval, 3 mm long and 2 mm wide, Brown N200A.

Pests and diseases:

*Tradescantia Andersoniana* Group is known to be susceptible viruses, aphids, and spider mites. The new cultivar has no known resistances but has shown no problems in Canby, Oreg.

I claim:

1. A new and distinct form of *Tradescantia* plant substantially as shown and described.

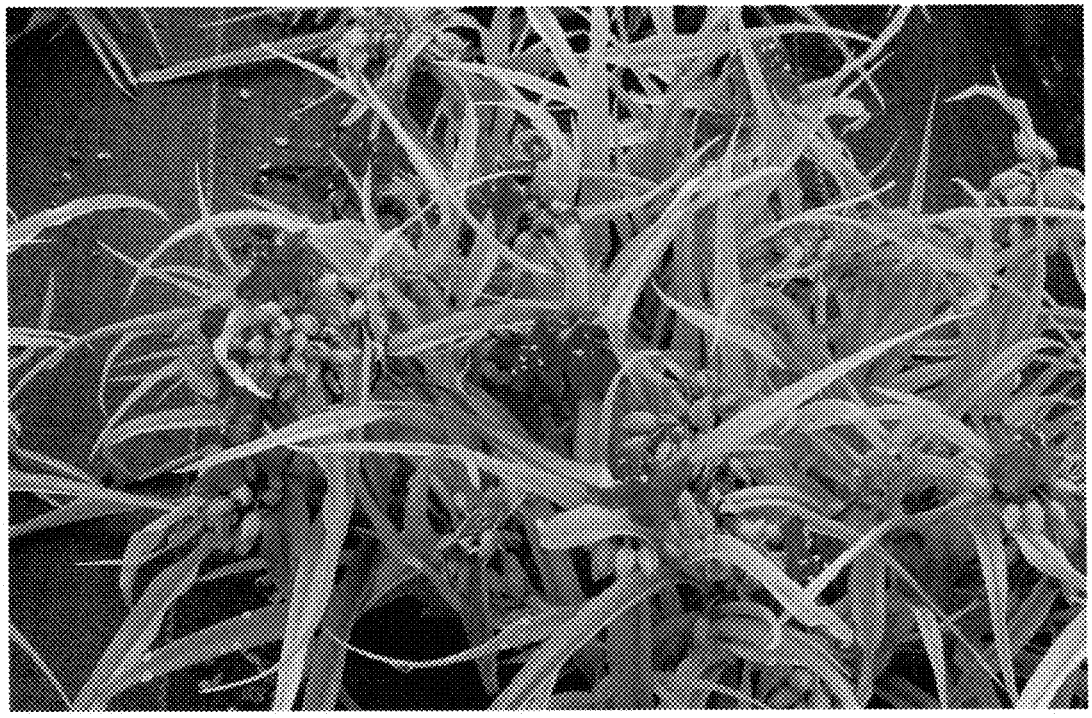

* * * * *